United States Patent
Subbiah

(12) 
(10) Patent No.: US 6,331,551 B1
(45) Date of Patent: Dec. 18, 2001

(54) METHODS OF TREATING MICROBIAL INFECTION AND THERAPEUTIC FORMULATIONS THEREFOR

(76) Inventor: Ven Subbiah, R. J. Reynolds Tobacco Company, Avoca Division, P.O. Box 129, Avoca Rd., Merry Hill, NC (US) 27957

( * ) Notice: Subject to any disclaimer, the term of this patent is extended or adjusted under 35 U.S.C. 154(b) by 0 days.

(21) Appl. No.: 09/711,700

(22) Filed: Nov. 13, 2000

Related U.S. Application Data

(62) Division of application No. 09/094,058, filed on Jun. 9, 1998, now Pat. No. 6,150,381.

(51) Int. Cl.$^7$ .......................... A01N 43/40; A61K 31/44; A61K 6/00; A61K 7/00
(52) U.S. Cl. ........................................ 514/340; 424/401
(58) Field of Search ............................. 514/340; 424/401

(56) References Cited

U.S. PATENT DOCUMENTS

| | | | |
|---|---|---|---|
| 3,060,172 | 10/1962 | Teague et al. . | |
| 3,952,099 | 4/1976 | Smith | 424/227 |
| 4,130,667 | 12/1978 | Smith | 424/361 |
| 4,446,145 | 5/1984 | Van Bever | 424/273 |
| 4,537,776 | 8/1985 | Cooper | 514/424 |
| 4,837,378 | 6/1989 | Borgman | 424/81 |
| 4,970,163 | 11/1990 | Farbood et al. | 435/255 |
| 5,155,029 | 10/1992 | Farbood et al. | 435/125 |
| 5,212,078 | 5/1993 | Farbood et al. | 435/126 |
| 5,247,100 | 9/1993 | Gerke et al. | 549/299 |
| 5,525,728 | 6/1996 | Schneider et al. | 549/299 |
| 6,150,381 | * 11/2000 | Subbiah | 514/430 |

FOREIGN PATENT DOCUMENTS

| | | |
|---|---|---|
| 0 419 026 A1 | 10/1990 | (EP) . |
| 747048 A2 | 11/1996 | (EP) . |
| 01311018 | 12/1989 | (JP) . |
| 10298070 | 11/1998 | (JP) . |
| WO9014764 | 12/1990 | (WO) . |
| WO 96/20704 | 7/1996 | (WO) . |

OTHER PUBLICATIONS

Banthorpe et al.; Accumulation of the Anti–Fungal Diterpene Sclareol by Cell Cultures of Salvia Sclarea and Nicotiana Glutinosa, *Phytochemistry*, 29(7):2145–2148 (1990).
Chackalamannil et al.; An efficient Synthesis of Wiedendiol–A from Sclareolide, *Tetrahedron Letters*, 36(30):5315–5318 (1995).
González et al.; A First Study of Antibacterial Activity of Diterpenes isolated from some Salvia Species (*Lamiaceae*), *Biochemical Systematics and Ecology*, 17(4):293–296 (1989).
González et al.; Minor Quinone Methide Diterpenoids from the Roots of *Salvia Texana, Journal of Natural Products*, 52(6):1231–1236 (1989(.

González et al.; New Diterpenes from *Salvia Texana*. Chemical and Biogenetic Aspects, *Tetrahedron*, 45(16):5203–5214 (1989).
González et al.; Flavonoids from *Salvia Texana, Phytochemistry*, 28(10):2871–2872 (1989).
Hanson; Diterpenoids, *Nat. Prod. Rep.*, 13:59–71 (1996).
Martres et al.; A Short and Practical Synthesis of (+)–Amberketal and (–)–epi–8–Amberketal from Natural (–)–Sclareol, *Tetrahedron Letters*, 34(50):8081–8084 (1993).
Sabri et al.; Abietane Diterpene Quinones from the Roots of *Salvia verbenaca* and *S. lanigera, Planta Medica*, 55 (1989).
Sharma, et al.; A Review on Clary Sage (*Salvia Sclarea* L.), *Cromap*, 7(1):39–48 (1985).
Topcu et al.; Abietane and Rearranged Abietane Diterpene from *Salvia montbretii, Journal of Natural Products*, 59:734–737 (1996).
Uluelen et al.; Norditerpenoids and Diterpenoids from *Salvia multicaulis* with Antituberculous Activity, *Journal of Natural Products*, 60(12):1275–1280 (1997).
Ulubelen et al.; Terpenoids from *Salvia Sclarea, Phytochemistry*, 36(4):971–974 (1994).
Wolf–Rainer Abraham, Microbial Hydroxylation of Sclareol, *Phytochemistry*, 36(6):1421–1424 (1994).
Harrison's Principles of Internal Medicine, 14$^{th}$ Edition, pp. 313–315.
Vichkanova et al.; Antimicrobial activity of root extracts of Salvia suppl., *Rastitel'nye Resursy*,, 10(3):389–395 (1974) Abstract Only #3111.
Crisan et al.; Investigations on fungistatic and fungicidal action of some extracts and volatile oils from medicinal plants, *Contributii Botanice*, 171–179 (1975) Abstract Only #3112.
Dobrynin et al.; Antimicrobial Substance of *Salvia officinalis, Khimiya Prirodnykh Soedinenii*, No. 5 686–687 (1976) Abstract Only #3113.
China, Chinese Academy of Medical Sciences; Correlations between phylogeny, chemical constituents and pharmaceutical aspects of plants and their applications in drug research (Part 1), *Acta Botanica Sinica* 19(3) 172–181 (1977) Abstract Only #3114.
Sinha et al.; Antibacterial activity of volatile oils from some indigenous plants, *Indian Journal of Experimental Biology*, 15(4)339–340 (1977) Abstract Only #3115.

(List continued on next page.)

*Primary Examiner*—Avis M. Davenport
(74) *Attorney, Agent, or Firm*—Myers Bigel Sibley & Sajovec

(57) ABSTRACT

Active compounds including sclareol-like and sclareolide-like compounds are usefull in methods of treating a wide variety of conditions and disorders, including those disorders caused by microbial (e.g., fungal and bacterial) infections, as well as those conditions and disorders caused by other mechanisms (e.g., activation of the adenylyl cyclase system). Pharmaceutical and cosmetic formulations comprising these active compounds are also useful in treating these disorders. One disorder that may be treated by the methods and formulations of the present invention is acne.

41 Claims, No Drawings

OTHER PUBLICATIONS

Vichkanova et al.; Prospects of search for antimicrobial substances among quinones of plant origin, *Rastitel'nye Resursy*, 15(2):167–177 (1979) Abstract Only #3116.

Cherevatyi et al.; Comparative evaluation of the antibacterial action of different extracts from *Salvia officinalis*, *Rastitel'nye Resursy* 16(1):137–139 (1980) Abstract Only #3117.

Miski et al.; Antibacterial Activity studies of flavonoids from *Salvia palaestina*, *Journal of Natural Products*, 46(6):874–875 (1983) Abstract Only #3118.

Ulubelen et al.; Terpenoids from *Salvia palaestina*, *Phytochemistry*, 24(6):1386–1387 (1985) Abstract Only #3119.

Honda et al.; Isolation of an antidermatophytic substance from the root of *Salvia miltiorrhiza*, *Chemical & Pharmaceutical Bulletin*, 36(1):408–411 (1988) Abstract Only #3120.

Steinmetz et al.; Transmitssion and scanning electromicroscopy study of the action of sage and rosemary essentials oils and eucalyptol on *Candida albicans*, *Mycoses*, 31(1):40–51 (1988) Abstract Only #3121.

Ulubelen et al.; Diterpenoids from the roots of *Salvia hypargeia*, *Journal of Natural Products*, 51(6):1178–1183 (1988) Abstract Only #3122.

González et al.; Abietane diterpenes with antibiotic activity from the flowers of *Salvia canariensis*. Reaction of galdosol with diazomethane, *Canadian Journal of Chemistry*, 67(2):208–212 (1989) Abstract Only #3123.

Sabri et al.; Two new rearranged abietane diterpene quinones from *Salvia aegyptiaca L.*, *Journal of Organic Chemistry*, 54(17):4097–4099 (1989) Abstract Only #3124.

González et al.; A first study of antibacterial activity of diterpenes isolated from some Salvia species (*Lamiaceae*), *Bio–chemical Systematics and Ecology*, 17(4):293–296 (1989) Abstract Only #3125.

Darias et al.; Cytostatic and antibacterial activity of some compounds isolated from several *Lamiaceae* species from the Canary Islands, *Planta Medica*, 56(1):70–72 (1990) Abstract Only #3126.

Mishra et al.; Fungitoxicity of essential oil of *Amomum subulatum* against *Asperigillus flavus*, *Economic Botany*, 44(4):530–533 (1990) Abstract Only #3127.

Dentali et al.; Potential antiinfective agents from *Eriodictyon angusifolium* and *Salvia apiana*, *International Journal of Pharmacognosy* 30(3):223–231 (1992) Abstract Only #3128.

Hoffmann et al.; Potential antimicrobial activity of plants from the southwestern United States, *International Journal of Pharmacognosy*, 31(2):101–115 (1993) Abstract Only #3129.

Pereda–Miranda et al.; A novel antimicrobial abietane–type diterpene from *Salvia albocaerulea*, *Planta Medica*, 58(2):223–224 (1992) Abstract Only #3130.

C. Demetzos; Chemical Analysis and Antimicrobial Activity of the Resin Ladano, of its Essential Oil and of the Isolated Compounds, (XP–002118269) *Planta Med.* 65:76–78 (1999).

A. Ulubelen et al.; Terpenoids From *Salvia Sclarea*, (XP–002118270) *Phytochemistry* 36, No. 4:971–974.

* cited by examiner

METHODS OF TREATING MICROBIAL INFECTION AND THERAPEUTIC FORMULATIONS THEREFOR

RELATED APPLICATIONS

This application is a divisional of U.S. application Ser. No. 09/094,058, filed Jun. 9, 1998, and now U.S. Pat. No. 6,150,381 the disclosure of which is incorporated herein in its entirety.

FIELD OF THE INVENTION

The invention relates to pharmaceutical formulations and cosmetic formulations useful for treating a wide variety of conditions and disorders, including formulations and methods for providing antimicrobial (e.g., antibacterial and antifungal) treatment to subjects in need of such treatment.

BACKGROUND OF THE INVENTION

Pathogenic microbes, including bacteria, fungi, protozoae, and viruses, have a profound effect on human health and well-being. In particular, bacterial and fungal infections are known to cause myriad human disorders, ranging from systemic and life-threatening diseases such as tuberculosis and pneumonia, to localized, discomfort-causing and appearance-altering conditions such as acne. The identification of therapeutic compounds useful in the treatment of microbial infections of all severities and modalities is a long-standing and potentially never-ending goal of medicine and pharmacology, made all the more difficult by the resistance of certain microbes to pharmaceutical inactivation. Certain anti-microbial agents are proposed in Hanson, *Nat. Prod. Rep.*, 13, 59–71 (1996); Banthorpe et al., *Phytochem.* 29(7), 2145–2148 (1990); and Ulubelen et al., Phytochem., 36(4), 971–974 (1994). Dermatological infections and disorders, in particular, may be contrary to effective treatment with pharmaceutical or cosmetic compounds in view of the barrier function of the skin and the difficulty of drug or cosmetic absorption thereby.

Although there are several factors that are thought to cause the skin disorder generally known as acne, one known causative factor is the presence of bacteria in the follicular canal of the skin. Within the follicular canal are bacteria which are indigenous to the follicular lining. One example of this bacteria is the anaerobic, gram positive *Propionibacterium acnes*. It is thought that *P. acnes* lives in symbiosis on the keratin lined follicular canal. P. acnes ingests the sebum produced from the sebocytes of the sebaceous glands. This nascent sebum is largely lipid in composition and also contains DNA, RNA, proteins, and other cellular components that result from the breakdown of sebocytes themselves. The *P. acnes* organisms, which are highly lipophilic, feed on the nascent sebum. It has been shown that *P. acnes* is found only in sebaceous-rich areas. If the nutrients increase due to an active and large sebaceous system, then colonization and high growth rates of *P. acnes* will occur. Resident bacterial flora will produce biologically active molecules such as histamine, extracellular enzymes, and peptides which may be responsible for the chemotaxis of the inflammatory infiltrate in acne vulgaris. Since the follicular lining in the pilosebaceous unit is intact, it has been theorized that if colonization of *P. acnes* occurs in sufficient numbers, they may produce initiating autogenic molecules that promote the initiating of inflammation. *P. acnes* can produce proteinases, lipase, and hyaluronate lyase all of which may serve as the catalysts or initiators of the inflammatory infiltrate, which has been shown to be composed of neutrophils and lymphocytes.

Gram negative acne, sometimes called gram negative folliculitis when it extends to the neck, arms, legs, and trunk, is a form of an inflammatory papular, follicular, and pustular response to gram negative organisms including Enterobacter, Klebsiella, Escherichia, Proteus, Serratia, and Pseudomonas. The most characteristic lesion on the face is superficial pustules, or papulo-pustules (which is a combination of a papule and pustule). The face can show diffuse erythema and inflammation surrounding these pustules and juicy papules or papulo-pustules. Gram negative acne is usually highly resistant and usually occurs in patients who have bad inflammatory papular acne for long periods or who have been treated with long term oral administration of antibiotics such as tetracycline, erytiromycin, or minocycline or topical antibiotics such as topical clindamycin or topical erytiromycin. Subsequent to the oral administration tetracycline or erythromycin, oral administration of amoxicillin, ampicillin, and trimethoprinsulfomethoxazole has been shown to be effective in treating this disease. Poli, F., Prost, C., Revuz, J., *Gram-negative Folliculitis, Ann. Dermatol. Venereol.*, 115:797–800, 1988.

A number of topical and systemic therapeutic treatments are presently known for treating acne. Some of the topical treatments that are presently employed are: topical erythromycin, clindamycin, benzoyl peroxide, sulfur, resorcinol, sulfosalicylate, salicylic acid, and retinoin (Retin-A®).

Benzoyl peroxide, $(C_6H_5CO)_2O_2$ ("BZP"), is a potent nontoxic oxidant which has long been used for treatment of dermatological lesions and known to be an effective antimicrobial and anti-keratolytic agent useful, for example, in the treatment of acne. Difficulties noted with BZP preparations have included BZP chemical instability. In its particulate solid form, BZP has been found to be generally more stable than its dissolved form. However, when a preparation containing BZP particles is utilized to treat dermatological lesions, the BZP particles eventually contacting the skin may have adverse irritative effects. These adverse effects appear to result, at least in part, from the excessive concentrations of BZP at skin areas in contact with BZP particles. Methods of avoiding such adverse effects while still effectively utilizing BZP therapeutically are long-sought. Still other topical treatments for acne using anti-bacterials are described in the following U.S. patents: an azole derivative in conjunction with benzoyl peroxide, U.S. Pat. No. 4,446,145, and metronidazole in a special gel as described in U.S. Pat. No. 4,837,378.

Aside from treatments mentioned above, some additional systemic treatments for acne that are presently employed are: oral tetracycline; oral erythromycin; minocycline; doxycycline; oral trimethoprim-sulfamethoxazole and isotretinoin (ACCUTANE®).

It would be desirable to provide methods of providing antimicrobial (e.g., antibacterial and antifungal) treatment, as well as treatment for other conditions and disorders caused by other mechanisms to subjects in need of such treatment, and cosmetic and pharmaceutical formulations useful in such treatments.

SUMMARY OF THE INVENTION

The present invention provides methods and formulations (both cosmetic and pharmaceutical) useful in treating a wide variety of disorders and conditions, including those disorders and conditions caused by bacterial and fungal infection in humans and animals. The methods and formulations of the present invention are useful in treating undesirable conditions or disorders caused by, for example, microorganisms selected from the group consisting of *Enterobacter aerogens, Propionibacterium acnes, Pseudomonas aeruginosa, Escherichia coli, Bacillus subtilis Agrobacterium tumefaciens, Staphylococcus aureus, Saccharomyces cerevisiae, Candida kefyr, Aspergillus flavus* and *Penicillium notatum*. The methods and formulations of the present invention are particularly useful in treating undesirable skin conditions such as, for example, acne vulgaris, preadolescent acne, acne rosacea (now known as rosacea), premenstrual acne, acne venenata, acne cosmetica, pomade acne, acne detergicans, acne cosmetica, acne excoriee, gram negative acne, steroid acne, acne conglobata, or nodulocystic acne. The present invention can also be used for topically treating certain types of dermatitis, e.g. perioral dermatitis, seborrheic dermatitis, gram negative folliculitis, sebaceous gland dysfunction, hidradenitis suppurativa, pseudofolliculitis barbae, folliculitis and dermatophyte infections (e.g., such as ringworm, athletes foot, and jock itch). Microbes present on the skin, particularly when allowed to proliferate in moist skin areas, are thought to be causes of objectionable body odor. The prevention and amelioration of such objectionable body odor in those susceptible thereto is also an objective of the present invention.

Accordingly, the present invention relates to a method of treating conditions and disorders caused by microbial infections, as well as other conditions and disorders caused by other mechanisms, in a subject in need of such treatment. The method comprises administering to the subject an active compound of the present invention (i.e., a sclareol-like or a sclareolide-like compound), in an amount effective to treat the disorder. One embodiment of the present invention is a method of treating a skin condition caused by a bacterial or fungal infection in a subject in need of such treatment, comprising contacting the skin of the subject with an effective amount of an active compound of the present invention, including, sclareolide, sclareol, and the cosmetically acceptable analogs and salts thereof. The compound may be provided to the subject in a cosmetic formulation, which formulations are also described herein as embodiments of the invention. Another embodiment of the invention involves a method of using a sclareolide-like compound to selectively activate second- messenger pathways that are involved in causing certain conditions and disorders, particularly those disorders and conditions associated with activation of the adenylyl cyclase system.

DETAILED DESCRIPTION OF THE INVENTION

The "active compounds of the present invention" include sclareol-like and sclareolide-like compounds. Sclareol-like compounds are diterpene compounds, and include, for example, sclareol, 13-episclareol, ferruginol, salvipisone, aethopisome, neoclerodane, sagequinone, romulogarzone, ortho-benzoquinone, para-benzoquinone, and clariol. Other sclareol-like compounds include abietane and icetexane diterpenoids, languidulane diterpene, paryin and pimarine diterpenes, methylene quinone diterpenoids, manoyl norditerpenoids, multicaulin, salvipimarone and pimarane diterpenoid. See, for example, the types of compounds set forth in Gonzalez et al., *Can. J. Chem.* 67(2), 208–212 (1989); Eanthorpe et al., *Phytochem.* 29, 2145–2148(1990); Kouzi et al., *Helv. Chim. Acta.* 73(8), 2157–2164 1990); Abraham, *Phytochem.* 36(6) 1421–1424(1994); Ulubelen et al. *Phytochem.* 36(4), 971–974 (1994); Hanson, *Nat. Prod. Rep.*, 13, 59–71 (1996) and Topcu et al., *J. Nat. Prod.* 59, 734–737 (1996). Sclareolide-like compounds are fused-ring diterpene compounds that may be derived from sclareol by chemical or biological techniques known to those skilled in the art; and include, for example, sclareolide, ambrox, and wiedenol. See, for example, the types of compounds set forth in Hanson, *Nat. Prod. Rep.* 13, 59–71 (1996); Chackalamanni et al., *Tetrahedron Letters* 36, 5315–5318 (1995); Barrero et al., *Tetrahedron Letters* 35, 2945–2948 (1994); Martres et al. *Tetrahedron Letters* 34, 801–8084 (1993) and Barrero et al., *Tetrahedron* 49(5), 10405–10412 (1993). The active compounds typically are cosmetically or pharmaceutically acceptable analogs, derivatives, or salts of sclareol or sclareolide. In the practice of the present invention, the active compounds may alternatively be substituted with alkyl (both unsaturated and saturated, and branched and unbranched, such as methyl, ethyl, or isopropyl), aryl, halogen, hydroxy, alkoxy, and amino groups, as will be apparent to those skilled in the art. Additionally, any of the active compounds of the present invention may be present as an optical isomer, or chiral compound, or as a mixture of optical isomers and chiral compounds.

Sclareol is an important bioactive diterpene obtained from clary sage (*Salvia sclarea* L.). This diterpene is not widely distributed and the most convenient sources.are flower heads of clary sage plant. Sclareol is obtained by solvent extraction of clary sage. U.S. Pat. No. 3,060,172 describes a process for the isolation of sclareol from clary sage. See also, U.S. patent application Ser. No. 08/92,081, filed Jan. 31, 1997, and 08/824,147, filed Mar. 25, 1997, which applications are incorporated herein in their entirety by reference. Sclareolide is prepared by either chemical oxidation followed by lactonization of sclareol or by biotransformation of sclareol using a yeast strain. Exemplary methods of producing sclareolide include those methods disclosed in U.S. Pat. Nos. 5,525,728 to Schneider et al., U.S. Pat. No. 5,247,100 to Gerke et al., and German Patent Application DE 3942358 to Gerke et al. Briefly, these processes use a ruthenium catalyst and an oxidation step to convert sclareol into a crude sclareolide product. Other exemplary methods of converting sclareol to sclareolide that are more commonly used include the biotransformation and fermentation methods described in U.S. Pat. Nos. 4,970,163 and 5,212,078, both to Farbood et al. Sclareolide produced by these described methods is normally provided in wet or dry cake form, and is generally from about 90% to 95% pure. Sclareolide has also been reported to have therapeutic properties. See, PCT Application No. WO 06/00704 to Braquet et al. The disclosures of these patents setting forth methods of producing sclareolide from sclareol are incorporated herein by reference in their entirety.

The active compounds of the present invention have antimicrobial (e.g., antibacterial and antifungal) activity These compounds are useful for the treatment of conditions including, but not limited to, acne vulgaris, preadolescent acne, rosacea, premenstrual acne, acne venenata, acne cosmetica, pomade acne, acne detergicans, acne cosmetica, acne excorie, gram negative acne, steroid acne, acne conglobata, or nodulocystic acne. The present invention can also be used for topically treating certain types of dermatitis, e.g. perioral dermatitis, seborrheic dermatitis, gram negative folliculitis, sebaceous gland dysfunction, hidradenitis suppurativa, pseudofolliculitis barbae, folliculitis and dermatophyte infections (e.g., such as ringworm, athletes foot, and jock itch). The compounds are also useful in methods of preventing or ameliorating undesirable body odor. Sclareolide-like compounds (in particular, sclareolide) evaluated using the techniques described in Bencherif et al., *JPET* 279, 1413–1421 (1996) are determined to exhibit a profile for inhibition of human nicotinic receptor function similar to forskolin (which is well established as an activator of adenylyl cyclase).

Subjects to be treated by the methods of the present invention are typically human subjects, although the methods of the present invention may be useful with any suitable subjects known to those skilled in the art, and particularly mammalian subjects including, in addition to humans, horses, cows, dogs, rabbits, fowl, sheep, and the like, for veterinary purposes.

The present invention provides cosmetic and pharmaceutical formulations comprising the active compounds (including the pharmaceutically acceptable salts thereof), in pharmaceutically or cosmetically acceptable carriers for oral, rectal, topical, buccal, parenteral, intramuscular, intradermal, or intravenous, and transdermal administration. In a preferred embodiment of the invention, the active compound may be administered to the subject as a topical, cosmetic formulation comprising (a) an active compound of the present invention and (b) a cosmetically acceptable carrier. The active compounds may be formulated for administration as cosmetic formulations for the treatment of a variety of conditions. These cosmetic formulations may take the form of, for example, a liquid, lotion, aerosol, cream, gel or ointments. In a preferred embodiment of a method of the present invention, an active compound of the present invention or a pharmaceutical or cosmetic formulation comprising the active compound is contacted with the skin of a subject suffering from a skin disorder caused by bacterial or fungal infection.

In the manufacture of a pharmaceutical or cosmetic formulation according to the invention, the active compounds (including the physiologically acceptable salts thereof) are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular., intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable apparatus, the compound in a free-flowing form, such as a powder or granules optionally mixed with a binder, lubricant, inert diluent, and/or surface active/dispersing agent(s). Molded tablets may be made by molding, in a suitable apparatus, the powdered compound moistened with an inert liquid binder.

Formulations suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

Topical cosmetic formulations suitable for topical application to the skin are particularly preferred, and may take the form of an ointment, cream, lotion, paste, gel, spray, aerosol, lotion, shampoo, foam, cream, gel, ointment, salve, milk, stick, spray, balm, emulsion, powder, solid or liquid soap, or oil. Such topical formulations comprise the active compound and a cosmetically acceptable carrier or medium. The cosmetically acceptable carrier generally comprises water or of a mixture of water and at least one organic solvent which is physiologically acceptable for the purpose of a topical application. Among these solvents, exemplary are acetone, $C_1$–$C_4$ lower alcohols such as ethanol and isopropyl alcohol, alkylene glycols such as ethylene glycol and propylene glycol, ethylene glycol monomethyl, monoethyl or monobutyl ethers, the monoethyl ethers of propylene glycol and of dipropylene glycol, the $C_1$–C4 alkyl esters of short-chain acids and polytetrahydrofuran ethers. When these are indeed present, such solvents preferably constitute from 1% to 80% by weight of the total weight of the formulation.

Depending on the intended application of the subject formulations, one skilled in the art can easily select the particular compounds and adjuvants that are necessary and characteristically employed to prepare those formulations. Among these adjuvants or additives, especially representative are preservatives, stabilizing agents, pH regulators, osmotic pressure modifiers, emulsifying agents, sunscreen agents, antioxidants, fragrances, colorants, anionic, cationic, nonionic, amphoteric or zwitterionic surface-active agents or mixtures thereof, polymers, and the like.

A topical formulation of the present invention, in addition to the active compound or the pharmaceutically acceptable salt thereof and the cosmetically acceptable medium or carrier, may also include an agent which enhances penetration of an active ingredient through the skin. Exemplary agents which increase skin penetration are disclosed in the following U.S. patents all of which are incorporated herein by reference: U.S. Pat. No. 4,537,776 (a binary combination of N-(hydroxyethyl)pyrrolidone and a cell-envelope disordering compound); U.S. Pat. No. 4,130,667 (using a sugar ester in combination with a sulfoxide or phosphine oxide); and U.S. Pat. No. 3,952,099 (using sucrose monooleate, decyl methyl sulfoxide, and alcohol). See also Manou et al., *Acta Horticulture* 344, 361–69 (1993).

Other exemplary materials that increase skin penetration are surfactants or wetting agents which include the following: polyoxyethylene sorbitan mono-oleoate (Polysorbate 80); sorbitan monooleate (Span 80); p-isooctyl polyoxyethylene-phenol polymer (Triton WR-1330); polyoxyethylene sorbitan tri-oleate (Tween 85); dioctyl sodium sulphosuccinate; and sodium sarcosinate (Sarcosyl NL-97); and other pharmaceutically acceptable surfactants.

The pharmaceutically or cosmetically acceptable carrier may be thickened using thickening agents typically employed in cosmetics or in pharmaceuticals. Among these thickening agents, particularly exemplary are cellulose and derivatives thereof such as cellulose ethers, heterobiopolysaccharides such as xanthan gum, scleroglucans, and polyacrylic acids which either may or may not be crosslinked. The thickening agents are preferably present in proportions ranging from 0.1% to 5% by weight approximately relative to the total weight of the composition.

The dose of the compound administered to the subject in need of treatment is that amount effective to prevent the onset or occurrence of a disorder caused by microbial infection, or to treat the disorder caused by the microbial infection from which the subject suffers. By "effective amount," "therapeutic amount," or "effective dose," is meant that amount sufficient to elicit the desired pharmacological or cosmetic effects, thus resulting in effective prevention or treatment of the disorder.

Preferably, the purity of the active compounds of the present invention is greater than about 50% pure, usually greater than about 80% pure, often greater than about 90% pure, and more often greater than about 95%, 98%, or even 99% pure, with active compounds approaching 100% purity being used most often.

The effective concentration or dosage of any specific compound, the use of which is in the scope of present invention, will vary somewhat from compound to compound, patient to patient, and will depend upon the condition of the patient and the route of delivery. As a general proposition, the dosage of an active compound of the present invention at which therapeutic efficacy will be achieved may be low as about 10 mg/kg, but is often greater than 25 or 50 mg/kg, and typically greater than about 100 mg/kg. The dosage of the active compound may be as high as about 5000 mg/kg, but is typically less than about 1000 mg/kg, usually less than 750 mg/kg and frequently less than 500 mg/kg. Still higher dosages may potentially being employed for oral, topical, and/or aerosol administration. Toxicity concerns at the higher level may restrict intravenous dosages to a lower level such as up to about 100 mg/kg, all weights being calculated based upon the weight of the active base, including the cases where a salt is employed. Typically a dosage from about 10 mg/kg to about 50 mg/kg will be employed for intravenous or intramuscular administration. A dosage from about 10 mg/kg to about 50 mg/kg may be employed for oral administration. For topical administration, suitable concentrations of the active compound may be from 1000 mg/ml to about 5000 mg/ml.

Active compounds used in the present method of treating microbial infections may be administered in conjunction with another antimicrobial agent, such other anti-acne agents including, but not limited to, benzoyl peroxide.

The preferred regime or regimen of application comprises applying 1 g to 10 g of the composition to all or to certain parts of the skin, at a frequency of one to two applications per day, for 1 to 7 days per week, for a period of time of from 1 to 6 months or even longer.

The present invention is further illustrated by the following non-limiting experimental examples.

EXAMPLE 1

Evaluation of Antibacterial Properties of Sclareol and Sclareolide

The following seven bacteria were grown on nutrient agar slants for 48 hours at 37° C.: *Enterobacter aerogens, Propionibacterium acnes, Pseudomonas aeruginosa, Escherichia coli, Bacillus subtilis, Agrobacterium tumefaciens*, and *Staphylococcus aureus*.

A bacterial colony from each of the respective slants was suspended in 1 ml sterile deionized water. 0.1 ml of each cell suspension was evenly spread on nutrient agar plates (10× $10^5$ cells/ml). After 30 min, sclareol and sclareolide-impregnated disks were placed on bacteria-lawned plates. The sclareol and sclareolide used in this experiment were relatively pure samples (greater than 99% pure). Triplicate disks of (10, 100, 500, and 1000 ug/disk) of each sample was applied on to 6 mm diameter (0.3 mm thickness) filter paper disks and air dried. Controls were prepared with respective solvents. Plates were incubated for 24–48 hr at 37° C. The inhibition zones were measured and recorded after 15 hr, up to 48 hr.

The results of this experiment are summarized in Table 1, below. In general, sclareol was more active than sclareolide against the bacteria tested. The bacteria *P. acnes, S. aureus* and *E. aerogens* were found to be more sensitive to both sclareol and sclareolide treatment, while *P. aeruginosa* and *E. coli* were the least sensitive to both compounds. Both compounds were found to be more active against Gram positive bacteria, specifically, *S. aureus* and *P. acnes*.

TABLE 1

Effect of sclareol and sclareolide on selected bacterial cultures

| | Zone of inhibition | | | | | | | |
|---|---|---|---|---|---|---|---|---|
| | Sclareol (ug/disk) | | | | Sclareolide (ug/disk) | | | |
| | 10 | 100 | 500 | 1000 | 10 | 100 | 500 | 1000 |
| *E. aerogens* | + | +++ | +++ | +++ | + | ++ | +++ | +++ |
| *P. acnes* | + | +++ | +++ | +++ | + | +++ | +++ | +++ |
| *P. aeruginosa* | − | + | ++ | ++ | − | − | ++ | ++ |
| *E. coli* | − | − | + | ++ | − | − | + | ++ |
| *D. subtilis* | + | + | ++ | ++ | + | + | + | ++ |

TABLE 1-continued

Effect of sclareol and sclareolide on selected bacterial cultures

|  | Zone of inhibition | | | | | | | |
|---|---|---|---|---|---|---|---|---|
|  | Sclareol (ug/disk) | | | | Sclareolide (ug/disk) | | | |
|  | 10 | 100 | 500 | 1000 | 10 | 100 | 500 | 1000 |
| A. tumefaciens | + | ++ | +++ | +++ | + | ++ | +++ | +++ |
| S. aureus | + | ++ | +++ | +++ | + | ++ | +++ | +++ |

Legend for Table 1: +++ = High inhibition; ++ = moderate inhibition; + = low inhibition; − = non inhibition.

The results from these experiments illustrate that the active compounds of the present invention are effective in inhibiting bacteria associated with numerous human diseases, thereby demonstrating the effectiveness of administration of the active compounds of the present invention as a treatment for these diseases.

EXAMPLE 2

Antifungal Properties of Sclareol and Sclareolide

The yeast and fungi listed below in Table 2 were grown on potato dextrose agar (PDA) containing different concentrations of sclareol and sclareolide, according to the following method: sclareol or sclareolide (in powder form) was added to pre-measured amounts of PDA medium in petri plates, mixed thoroughly by tilting the petri plate from side to side, and allowed to solidify. The sclareol and sclareol used in preparing the petri plates was of greater than 99% purity. After solidification, the plates were inoculated with 5 mm disks, cut from the outer margin of the actively growing cultures of yeast and fungi and placed in the center of the plate in an inverted position in direct contact with the sclareol/sclareolide impregnated medium. The plates were incubated at 26° C. The plates were monitored periodically to estimate the minimum inhibitory concentration (MIC) based on the growth proliferation from the 5 mm inoculum disk.

The results were measured and recorded after 48 hr, up to one week. The results are tabulated in Table 2, below.

TABLE 2

Antifungal properties of sclareol and sclareolide on selected yeast and fungi

| Microorganism | MIC (ug/ml) | |
|---|---|---|
|  | Sclareol | Sclareolide |
| Saccharomyces cerevisiae | 500 | 500 |
| Candida kefyr | 100 | 400 |
| Aspergilus flavus | 1000 | 1000 |
| Penicillium notatum | 1000 | 1000 |

The results from this experiment illustrate that the active compounds of the present invention are effective in inhibiting the growth of fungi associated with certain human diseases or disorders, thereby demonstrating the effectiveness of administration of the active compounds of the present invention as a treatment for these diseases.

EXAMPLE 3

Summary of Results

A summary of the effects of sclareol and sclareolide against the bacteria and fungi tested in Examples 1 and 2 is provided in Table 3. The data is presented as the effect of sclareol and sclareolide on selected microbial cultures, in terms of minimum inhibitory concentration, as measured in μg/ml.

TABLE 3

Effect of Sclareol and Sclareolide on selected microbial cultures

| Microbe | MIC (ug/ml) | |
|---|---|---|
|  | Sclareol | Sclareolide |
| E. aerogens | 10 | 10 |
| P. acnes | 40 | 40 |
| P. aeruginosa | 100 | 500 |
| E. coli | 500 | 500 |
| B. subtilis | 10 | 10 |
| A. tumefaciens | 10 | 10 |
| S. aureus | 50 | 50 |
| Saccharomyces | 500 | 500 |
| Candida kefyr | 100 | 400 |
| Aspergillus flavus | 1000 | 1000 |
| Penicillium notatum | 1000 | 1000 |

In the specification and examples, there have been disclosed preferred embodiments of the invention. Although specific terms are employed in these examples, they are used in a generic and descriptive sense only and not for the purpose of limitation, the scope of the invention being defined by the following claims and their equivalents.

That which is claimed:

1. A cosmetic formulation for treating a skin disorder caused by a microbial infection, comprising a sclareol-like or a sclareolide-like compound in an amount sufficient to treat said skin disorder, in a cosmetically acceptable carrier.

2. A cosmetic formulation according to claim 1, wherein said sclareol-like compound is selected from the group consisting of sclareol, 13-episclareol, ferruginol, salvipisone, aethopisome, neoclerodane, sagequinone, romulogarzone, ortho-benzoquinone, para-benzoquinone, and clariol.

3. A cosmetic formulation according to claim 1, wherein said sclareol-like compound is selected from the group consisting of abietane diterpenoids, icetexane diterpenoids, languidulane diterpenes, paryin diterpenes, pimarine diterpenes, methylene quinone diterpenoids, manoyl norditerpenoids, pimarane diterpenoids, multicaulin, and salvipimarone.

4. A cosmetic formulation according to claim 1, wherein said sclareol-like compound is sclareol.

5. A cosmetic formulation according to claim 1, wherein said sclareol-like compound is selected from the group consisting of sclareolide, ambrox, and wiedenol.

6. A cosmetic formulation according to claim 1, wherein said sclareolide-like compound is sclareolide.

7. A cosmetic formulation according to claim 1, wherein said formulation is suitable for topical application to skin and is in a form selected from the group consisting of ointments, creams, lotions, pastes, gels, sprays, aerosols, lotions, shampoos, foams, salves, milks, sticks, balms, emulsions, powders, solid or liquid soaps, and oils.

8. A cosmetic formulation according to claim 1, wherein said cosmetic formulation is a cream.

9. A cosmetic formulation according to claim 1, wherein said formulation is a lotion.

10. A cosmetic formulation according to claim 1, wherein said formulation is an aerosol.

11. A cosmetic formulation according to claim 1, wherein the formulation comprises from 0.1 M to 0.2M of the sclareol-like or sclareolide-like compound in a buffered aqueous solution.

12. A cosmetic formulation according to claim 1, wherein the cosmetically acceptable carrier is water.

13. A cosmetic formulation according to claim 1, wherein the cosmetically acceptable carrier is a solution comprising water and at least one organic solvent.

14. A cosmetic formulation according to claim 13, wherein the organic solvent is present in an amount from 1 to 80 percent by weight of the total weight of the formulation.

15. A cosmetic formulation according to claim 1, further comprising a wetting agent.

16. A cosmetic formulation according to claim 1, further comprising a thickening agent.

17. A cosmetic formulation according to claim 1, further comprising benzoyl peroxide.

18. A cosmetic formulation according to claim 1, wherein the concentration of the sclareol-like or sclareolide-like compound is from about 1000 mg/ml to about 5000 mg/ml.

19. A cosmetic formulation according to claim 1, wherein the sclareol-like or sclareolide-like compound is greater than about 90% pure.

20. A cosmetic formulation according to claim 1, wherein the sclareol-like or sclareolide-like compound is greater than about 95% pure.

21. A cosmetic formulation for treating a condition or disorder associated with activation of a second messenger pathway, the formulation comprising a sclareol-like or a sclareolide-like compound in an amount sufficient to treat said condition or disorder, in a cosmetically acceptable carrier.

22. A cosmetic formulation according to claim 21, wherein said second messenger pathway is the adenylyl cyclase system.

23. A cosmetic formulation according to claim 21, wherein said sclareol-like compound is selected from the group consisting of sclareol, 13-episclareol, ferruginol, salvipisone, aethopisome, neoclerodane, sagequinone, romulogarzone, ortho-benzoquinone, para-benzoquinone, and clariol.

24. A cosmetic formulation according to claim 21, wherein said sclareol-like compound is selected from the group consisting of abietane diterpenoids, icetexane diterpenoids, languidulane diterpenes, paryin diterpenes, pimarine diterpenes, methylene quinone diterpenoids, manoyl norditerpenoids, pimarane diterpenoids, multicaulin, and salvipimarone.

25. A cosmetic formulation according to claim 21, wherein said sclareol-like compound is sclareol.

26. A cosmetic formulation according to claim 21, wherein said sclareol-like compound is selected from the group consisting of sclareolide, ambrox, and wiedenol.

27. A cosmetic formulation according to claim 21, wherein said sclareolide-like compound is sclareolide.

28. A cosmetic formulation according to claim 21, wherein said formulation is suitable for topical application to skin and is in a form selected from the group consisting of ointments, creams, lotions, pastes, gels, sprays, aerosols, lotions, shampoos, foams, salves, milks, sticks, balms, emulsions, powders, solid or liquid soaps, and oils.

29. A cosmetic formulation according to claim 21, wherein said cosmetic formulation is a cream.

30. A cosmetic formulation according to claim 21, wherein said formulation is a lotion.

31. A cosmetic formulation according to claim 21, wherein said formulation is an aerosol.

32. A cosmetic formulation according to claim 21, wherein the formulation comprises from 0.1 M to 0.2M of the sclareol-like or sclareolide-like compound in a buffered aqueous solution.

33. A cosmetic formulation according to claim 21, wherein the cosmetically acceptable carrier is water.

34. A cosmetic formulation according to claim 21, wherein the cosmetically acceptable carrier is a solution comprising water and at least one organic solvent.

35. A cosmetic formulation according to claim 34, wherein the organic solvent is present in an amount from 1 to 80 percent by weight of the total weight of the formulation.

36. A cosmetic formulation according to claim 21, further comprising a wetting agent.

37. A cosmetic formulation according to claim 21, further comprising a thickening agent.

38. A cosmetic formulation according to claim 21, further comprising benzoyl peroxide.

39. A cosmetic formulation according to claim 21, wherein the concentration of the sclareol-like or sclareolide-like compound is from about 1000 mg/ml to about 5000 mg/ml.

40. A cosmetic formulation according to claim 21, wherein the sclareol-like or sclareolide-like compound is greater than about 90% pure.

41. A cosmetic formulation according to claim 21, wherein the sclareol-like or sclareolide-like compound is greater than about 95% pure.

* * * * *